US012161688B2

(12) United States Patent
Marom et al.

(10) Patent No.: US 12,161,688 B2
(45) Date of Patent: Dec. 10, 2024

(54) TREATMENT OF INFLAMMATORY BOWEL DISEASE WITH LONG ACTING GLATIRAMER AND ADIPOSE-DERIVED STEM CELLS

(71) Applicants: STEM CELL MEDICINE LTD., Jerusalem (IL); MAPI PHARMA LTD., Ness Ziona (IL)

(72) Inventors: Ehud Marom, Tel Aviv (IL); Nadav Bleich Kimelman, Tel Aviv (IL); Frida Grynspan, Mevasseret Zion (IL)

(73) Assignees: MAPI PHARMA LTD, Ness Ziona (IL); STEM CELL MEDICINE LTD., Jerusalem (IL)

( * ) Notice: Subject to any disclaimer, the term of this patent is extended or adjusted under 35 U.S.C. 154(b) by 744 days.

(21) Appl. No.: 16/311,073

(22) PCT Filed: Jun. 29, 2017

(86) PCT No.: PCT/IL2017/050722
§ 371 (c)(1),
(2) Date: Dec. 18, 2018

(87) PCT Pub. No.: WO2018/002930
PCT Pub. Date: Jan. 4, 2018

(65) Prior Publication Data
US 2021/0220428 A1 Jul. 22, 2021

Related U.S. Application Data

(60) Provisional application No. 62/356,543, filed on Jun. 30, 2016.

(51) Int. Cl.
*A61K 38/02* (2006.01)
*A61K 9/00* (2006.01)
*A61K 9/113* (2006.01)
*A61K 35/28* (2015.01)
*A61P 1/00* (2006.01)
*A61P 37/02* (2006.01)

(52) U.S. Cl.
CPC ............ *A61K 38/02* (2013.01); *A61K 9/0019* (2013.01); *A61K 9/113* (2013.01); *A61K 35/28* (2013.01); *A61P 1/00* (2018.01); *A61P 37/02* (2018.01)

(58) Field of Classification Search
CPC ........ A61K 38/02; A61K 35/28; A61K 9/113; A61K 9/0019
See application file for complete search history.

(56) References Cited

U.S. PATENT DOCUMENTS

| | | |
|---|---|---|
| 3,849,550 A | 11/1974 | Teitelbaum et al. |
| 5,981,589 A | 11/1999 | Konfino et al. |
| 6,048,898 A | 4/2000 | Konfino et al. |
| 6,054,430 A | 4/2000 | Konfino et al. |
| 6,214,791 B1 | 4/2001 | Arnon |
| 6,342,476 B1 | 1/2002 | Konfino et al. |
| 6,362,161 B1 | 3/2002 | Konfino et al. |
| 6,620,847 B2 | 9/2003 | Konfino et al. |
| 6,844,314 B2 | 1/2005 | Eisenbach-Schwartz |
| 6,939,539 B2 | 9/2005 | Konfino et al. |
| 8,008,258 B2 | 8/2011 | Aharoni et al. |
| 8,021,882 B2 | 9/2011 | Johnstone et al. |
| 8,216,566 B2 | 7/2012 | Paludan |
| 8,377,885 B2 | 2/2013 | Marom et al. |
| 8,404,866 B2 | 3/2013 | Schwartz |
| 8,642,331 B2 | 2/2014 | Sadiq |
| 8,679,834 B2 | 3/2014 | Lombardo |
| 8,703,180 B1 | 4/2014 | Stankus |
| 8,785,199 B2 | 7/2014 | Hotta |
| 8,796,226 B2 | 8/2014 | Marom et al. |
| 9,200,114 B2 * | 12/2015 | Marom ............... A61K 31/785 |
| 2007/0269413 A1 | 11/2007 | Serhan |
| 2008/0063687 A1 | 3/2008 | Chou et al. |
| 2009/0148419 A1 | 6/2009 | Gonzalez De La Pena |
| 2009/0191173 A1 | 7/2009 | Eisenbach-Schwartz |
| 2009/0291061 A1 | 11/2009 | Riordan |
| 2011/0008300 A1 | 1/2011 | Wouters |
| 2011/0129450 A1 | 6/2011 | Lazarov |
| 2012/0015891 A1 | 1/2012 | Marom et al. |
| 2012/0064098 A1 | 3/2012 | Consigny |
| 2012/0101061 A1 | 4/2012 | Gjorstrup |
| 2012/0164114 A1 | 6/2012 | Abbot |
| 2012/0164229 A1 | 6/2012 | Marom |
| 2012/0230966 A1 | 9/2012 | Crawford |
| 2013/0034524 A1 | 2/2013 | Agha-Mohammadi |
| 2013/0156725 A1 | 6/2013 | Marom |
| 2014/0037598 A1 | 2/2014 | Timothy |
| 2014/0140968 A1 | 5/2014 | Kadouri |

(Continued)

FOREIGN PATENT DOCUMENTS

| | | |
|---|---|---|
| CN | 103403150 A | 11/2013 |
| CN | 104130975 A | 11/2014 |

(Continued)

OTHER PUBLICATIONS

Nagaishi, K., et al. J. Gastroenterol; 50:280-286 (Year: 2015).*
Perez-Merino, E.M., et al. Vet J;206:385-390 (Year: 2015).*
Abramsky et al., (1982) Alpha-fetoprotein suppresses experimental allergic encephalomyelitis. J Neuroimmunol 2(1):1-7.
Aharoni et al., (2009) Transplanted myogenic progenitor cells express neuronal markers in the CNS and ameliorate disease in experimental autoimmune encephalomyelitis. J Neuroimmunol 215(1-2): 73-83.
Azevedo Margarida; "Promising Phase 1 Trial Results of Stem Cell Therapy in Progressive MS Patients Being Presented at AAN Meeting", Multiple Sclerosis News Today Apr. 19, 2016. Retrieved from: https://multiplesclerosisnewstoday.com/news-posts/2016/04/19/promising-phase-1-trial-results-stem-cell-therapy-progressive-ms-patients-presented-aan-meeting/ on Oct. 22, 2019; 6 pages.

(Continued)

*Primary Examiner* — Karen A. Canella
(74) *Attorney, Agent, or Firm* — ROTHWELL FIGG ERNST & MANBECK P.C.

(57) ABSTRACT

Methods for treating inflammatory bowel disease are provided, comprising administration of glatiramer acetate in a sustained-release depot form and administration of adipose-derived stem cells.

17 Claims, 4 Drawing Sheets

(56) References Cited

U.S. PATENT DOCUMENTS

| | | |
|---|---|---|
| 2014/0234272 A1 | 8/2014 | Vesey |
| 2014/0308745 A1 | 10/2014 | Sadiq |
| 2014/0315870 A1 | 10/2014 | Conget Molina |
| 2015/0030662 A1 | 1/2015 | Raghunath |
| 2015/0216908 A1 | 8/2015 | Lee |
| 2017/0065638 A1 | 3/2017 | Fraser |

FOREIGN PATENT DOCUMENTS

| | | | |
|---|---|---|---|
| CN | 104203901 A | 12/2014 | |
| EP | 1592384 B1 | 10/2012 | |
| EP | 1827108 B1 | 4/2015 | |
| WO | 2006057003 A2 | 6/2006 | |
| WO | 2006060779 A2 | 6/2006 | |
| WO | 2010045645 A1 | 4/2010 | |
| WO | 2011080733 A1 | 7/2011 | |
| WO | WO-2011087795 A2 * | 7/2011 | ........... A61K 31/137 |
| WO | 2017139795 A1 | 8/2017 | |
| WO | 2018002930 A1 | 1/2018 | |

OTHER PUBLICATIONS

Baer (2014) Adipose-derived mesenchymal stromal/stem cells: An update on their phenotype in vivo and in vitro. World J Stem Cells 6(3): 256-265.

Bai et al., (2010) Both cultured and freshly isolated adipose tissue-derived stem cells enhance cardiac function after acute myocardial infarction. Eur Heart J 31(4): 489-501.

Barhum et al., (2010) Intracerebroventricular transplantation of human mesenchymal stem cells induced to secrete neurotrophic factors attenuates clinical symptoms in a mouse model of multiple sclerosis. J Mol Neurosci 41(1): 129-137.

Ben-Nun et al., (1996) The autoimmune reactivity to myelin oligodendrocyte glycoprotein (MOG) in multiple sclerosis is potentially pathogenic: effect of copolymer 1 on MOG-induced disease. J Neurol. 243(4 Suppl 1): S14-S22.

Bolton et al., (1982) Immunosuppression by cyclosporin A of experimental allergic encephalomyelitis. J Neurol Sci 56(2-3): 147-153.

Bonab et al., (2012) Autologous mesenchymal stem cell therapy in progressive multiple sclerosis: an open label study. Curr Stem Cell Res Ther 7(6): 407-414.

Choi et al., (2011) Cell proliferation and neuroblast differentiation in the rat dentate gyrus after intrathecal treatment with adipose-derived mesenchymal stem cells. Cell Mol Neurobiol 31(8): 1271-1280.

Choudhery et al., (2014) Cryopreservation of whole adipose tissue for future use in regenerative medicine. J Surg Res 187(1): 24-35.

Cohen et al., (2007) Randomized, double-blind, dose-comparison study of glatiramer acetate in relapsing-remitting MS. Neurology 68(12): 939-944.

Constantin et al., (2009) Adipose-derived mesenchymal stem cells ameliorate chronic experimental autoimmune encephalomyelitis. Stem Cells 27(10): 2624-2635.

Croitoru-Lamoury et al., (2007) Human mesenchymal stem cells constitutively express chemokines and chemokine receptors that can be upregulated by cytokines, IFN-beta, and Copaxone. J Interferon Cytokine Res 27(1): 53-64.

Devitt et al., (2015) Successful isolation of viable adipose-derived stem cells from human adipose tissue subject to long-term cryopreservation: positive implications for adult stem cell-based therapeutics in patients of advanced age. Stem Cells Int 2015: 146421; 12 pages.

Doshi and Chataway (2016) Multiple sclerosis, a treatable disease. Clin Med (Lond) 16(Suppl 6): s53-s59.

Freedman et al., (2010) The therapeutic potential of mesenchymal stem cell transplantation as a treatment for multiple sclerosis: consensus report of the International MSCT Study Group. Mult Scler 16(4): 503-510.

Ghasemi et al., (2014) Transplantation of human adipose-derived stem cells enhances remyelination in lysolecithin-induced focal demyelination of rat spinal cord. Mol Biotechnol 56(5): 470-478.

Giacoppo et al., (2017) The transplantation of mesenchymal stem cells derived from unconventional sources: an innovative approach to multiple sclerosis therapy. Arch Immunol Ther Exp (Warsz) 65(5): 363-379.

Gong et al., (2012) Banking human umbilical cord-derived mesenchymal stromal cells for clinical use. Cell Transplant 21(1): 207-216.

Hayon et al., (2012) Platelet microparticles promote neural stem cell proliferation, survival and differentiation. J Mol Neurosci 47(3): 659-665.

Johnson et al., (1995) Copolymer 1 reduces relapse rate and improves disability in relapsing-remitting multiple sclerosis. Results of a phase III multicenter, double-blind, placebo-controlled trial. Neurology 45(7): 1268-1276.

Lin et al., (2012) Is CD34 truly a negative marker for mesenchymal stromal cells? Cytotherapy 14(10): 1159-1163.

Martino et al., (2010) Stem cell transplantation in multiple sclerosis: current status and future prospects. Nat Rev Neurol 6(5): 247-255.

Menard et al., (2013) Clinical-grade mesenchymal stromal cells produced under various good manufacturing practice processes differ in their immunomodulatory properties: standardization of immune quality controls. Stem Cells Dev 22(12): 1789-1801.

Mirabet et al., (2012) Use of liquid nitrogen during storage in a cell and tissue bank: contamination risk and effect on the detectability of potential viral contaminants. Cryobiology 64(2): 121-123.

Muraro et al., (2017) Long Term Outcomes after Autologous Hematopoietic Stem Cell Transplantation for Multiple Sclerosis. JAMA Neurol. Author manuscript; available in PMC Dec. 27, 2017. 19 pages.

Pisati et al., (2007) Induction of neurotrophin expression via human adult mesenchymal stem cells: implication for cell therapy in neurodegenerative diseases. Cell Transplant 16(1): 41-55.

Ra et al., (2011) Stem cell treatment for patients with autoimmune disease by systemic infusion of culture-expanded autologous adipose tissue derived mesenchymal stem cells. J Transl Med 9: 181; 12 pages.

Riordan et al., (2009) Non-expanded adipose stromal vascular fraction cell therapy for multiple sclerosis. J Transl Med 7: 29; 9 pages.

Scruggs et al., (2013) Age of the donor reduces the ability of human adipose-derived stem cells to alleviate symptoms in the experimental autoimmune encephalomyelitis mouse model. Stem Cells Transl Med 2(10): 797-807.

Sela et al., (1990) Suppressive activity of Cop-1 in EAE and its Relevance to Multiple Sclerosis. Bull Inst Pasteur 88: 303-314.

Shalaby et al., (2016) Adipose-derived mesenchymal stem cells modulate the immune response in chronic experimental autoimmune encephalomyelitis model. IUBMB Life 68(2): 106-115.

Shinmura et al., (2011) Pretreatment of human mesenchymal stem cells with pioglitazone improved efficiency of cardiomyogenic transdifferentiation and cardiac function. Stem Cells 29(2): 357-366.

Silva and Ferrari; Animal experimental models for understanding and treating Multiple Sclerosis. SMGroup, Dover, DE 19904, USA. Published: Aug. 18, 2016; 16 pages.

Silva Patricia; "Research on Faulty Stem Cells Suggests MS Patients Need Tailored Therapies". Multiple Sclerosis News Today, Apr. 4, 2017. Retrieved from: https://multiplesclerosisnewstoday.com/2017/04/04/study-on-faulty-multiple-sclerosis-stem-cells-suggests-patients-need-tailored-therapies/ on Oct. 22, 2019; 7 pages.

Soleimani et al., (2016) Stem Cell Therapy—Approach for Multiple Sclerosis Treatment. Arch Neurosci 3(1): e21564; 9 pages.

Sorensen et al., (1998) Intravenous immunoglobulin G reduces MRI activity in relapsing multiple sclerosis. Neurology 50(5): 1273-1281.

Stepien et al., (2016) Clinical Application of Autologous Adipose Stem Cells in Patients with Multiple Sclerosis: Preliminary Results. Mediators Inflamm 2016: 5302120; 6 pages.

Teitelbaum et al., (1996) Copolymer 1 inhibits chronic relapsing experimental allergic encephalomyelitis induced by proteolipid (56) References Cited

OTHER PUBLICATIONS protein (PLP) peptides in mice and interferes with PLP-specific T cell responses. J Neuroimmunol 64(2): 209-217.
Traktuev et al., (2008) A population of multipotent CD34-positive adipose stromal cells share pericyte and mesenchymal surface markers, reside in a periendothelial location, and stabilize endothelial networks. Circ Res 102(1): 77-85.
Tsuji et al., (2014) Adipose-derived stem cells: Implications in tissue regeneration. World J Stem Cells 6(3): 312-321.
Wilkins et al., (2009) Human bone marrow-derived mesenchymal stem cells secrete brain-derived neurotrophic factor which promotes neuronal survival in vitro. Stem Cell Res 3(1): 63-70.
Wolinsky et al., (2009) Glatiramer acetate treatment in PPMS: why males appear to respond favorably. J Neurol Sci 286(1-2): 92-98.
Zhu et al., (2013) Manual isolation of adipose-derived stem cells from human lipoaspirates. J Vis Exp (79): e50585; 10 pages.
Abcam (Jan. 10, 2016) Cryopreservation of mammalian cell lines video protocol. https://www.abcam.com/protocols/cryopreservation-of-mammalian-cell-lines-video-protocols (Year: 2016). 2 pages.
ClinicalTrials.gov Identifier: NCT02157064. Outcomes Data of Adipose Stem Cells to Treat Multiple Sclerosis. Sponsor: StemGenex. Retrieved from: https://clinicaltrials.gov/ct2/show/NCT02157064 on Mar. 15, 2017; 3 pages.
Primary progressive MS (PPMS), National Multiple Sclerosis Society, accessed Jan. 11, 2022, 7 pages.
Secondary progressive MS (SPMS), National Multiple Sclerosis Society, accessed Jan. 11, 2022, 7 pages.
Treatment procedure with stem cells. Swiss medica 21, regenerative medicine clinical center.Primary Progresive Multiple Sclerosis—Case 034. Retrieved from: http://www.startstemcells.com/Primary-Progresive-Multiple-Sclerosis-Case034.html on May 8, 2017. 7 pages.
Kazama (2016) Basic research and clinical application in mesenchymal stem cells. J Nihon Univ Med Ass 75(2): 61-66 English abstract.
Kira (2016) Recent Treatments for Multiple Sclerosis. The Journal of the Japanese Society for Internal Medicine 105 (5): 894-904 Machine translated abstract and details.
Liang Xingguang (2015) Clinical application of stem cell transplantation in the treatment of neurodegenerative diseases. Chinese Journal of Transplantation 9(4): 188-193—Machine translation of details and summary.
Nakayama and Kato (2013) Cell therapy using adipose-derived mesenchymal stromal cells: current status and perspectives. Japanese Journal of Transfusion and Cell Therapy 59(3): 450-456 Machine translated abstract.
English translation of decision of rejection dated Nov. 1, 2022 in JP Patent Application No. 2019-562579. 4 pages.
Aharoni, "Immunomodulation neuroprotection and remyelination—The fundamental therapeutic effects of glatiramer acetate: A critical review", Journal of Autoimmunity, (2014), 54: 81-92.
Aharoni et al., "Immunomodulatory Therapeutic Effect of Glatiramer Acetate on Several Murine Models of Inflammatory Bowel Disease", The Journal of Pharmacology and Experimental Therapeutics, (2006), vol. 318, No. 1, pp. 68-78.
Baer and Geiger, "Adipose-Derived Mesenchymal Stromal/Stem Cells: Tissue Localization, Characterization, and Heterogeneity", Stem Cells International, (2012) vol. 2012, Article ID 812693, 12 pages.
Boismenu and Chen, "Insights from mouse models of colitis", Journal of Leukocyte Biology, (2000), vol. 67(3): 267-278.
Bunnell et al., "Adipose-derived stem cells: isolation, expansion and differentiation", Methods (2008) vol. 45(2): 115-120.
Chinnadurai et al., "Challenges in animal modelling of mesenchymal stromal cell therapy for inflammatory bowel disease", World J Gastroenterol (2015), 21(16): 4779-4787.
Flores et al., "Stem cell therapy in inflammatory bowel disease: A promising therapeutic strategy?", World J Stem Cells, (2015), 7(2): 343-351.
Jung et al., "Human adipose-derived stem cells attenuate inflammatory bowel disease in IL-10 knockout mice", Tissue and Cell, (2015), 47(1): 86-93.
Neuhaus et al., "Pharmacokinetics and pharmacodynamics of the interferon-betas, glatiramer acetate, and mitoxantrone in multiple sclerosis", Journal of the Neurological Sciences, (2007), 259(1-2): 27-37.
Panés et al., "852 Cx601, Expanded Allogeneic Adipose-Derived Mesenchymal Stem Cells (eASC), for Complex Perianal Fistulas in Crohn's Disease: Results From a Phase III Randomized Controlled Trial", Gastroenterology, (2016), 150(4): Supplement 1, p. S181.
Shanahan "Inflammatory bowel disease: immunodiagnostics, immunotherapeutics, and ecotherapeutics", Gastroenterology, (2001), 120(3): 622-635.
Teitelbaum et al., "Suppression of experimental allergic encephalomyelitis by a synthetic polypeptide", Eur J Immunol, (1971), 1(4): 242-248.
Teitelbaum et al., "Suppression by several synthetic polypeptides of experimental allergic encephalomyelitis induced in guinea pigs and rabbits with bovine and human basic encephalitogen", Eur J Immunol, (1973), 3(5): 273-279.
Todd et al., "Mesenchymal Stem Cells as Vehicles for Targeted Therapies, in: Drug Discovery and Development—Present and Future" edited by Izet M. Kapetanovic, IntechOpen, (2011), DOI: 10.5772/29124, pp. 489-528.
Zuk et al., "Human Adipose Tissue Is a Source of Multipotent Stem Cells", Molecular Biology of the Cell, (2002), vol. 13(12): 4279-4295.
NHS, Crohn's disease—Treatment, retrieved from <https://www.nhs.uk/conditions/crohns-disease/treatment/>, page last reviewed: Apr. 22, 2021 (PDF copy 2 pages).
NHS, Anal fistula—Treatment, retrieved from <https://www.nhs.uk/conditions/anal-fistula/treatment/> page last reviewed: Jun. 18, 2019 (PDF copy 2 pages).
Han et al., Adipose-Derived Stromal Vascular Fraction Cells: Update on Clinical Utility and Efficacy, Critical Reviews in Eukaryot Gene Expression, 2015, 25(2): 145-152.
U.S. FDA grants Breakthrough Therapy Designation for Roche's investigational medicine ocrelizumab in primary progressive multiple sclerosis. Investor Update. Basel, Feb. 17, 2016. Retrieved from: https://www.roche.com/investors/updates/inv-update-2016-02-17.htm on Oct. 10, 2019; 5 pages.

\* cited by examiner

Figure 4

TREATMENT OF INFLAMMATORY BOWEL DISEASE WITH LONG ACTING GLATIRAMER AND ADIPOSE-DERIVED STEM CELLS

CROSS REFERENCE TO RELATED APPLICATION

This application is a 35 U.S.C. 371 National Phase Entry Application from PCT/IL2017/050722, filed Jun. 29, 2017, which claims the benefit of U.S. Provisional Patent Application No. 62/356,543 filed on Jun. 30, 2016, the disclosures of which are incorporated herein in their entirety by reference.

FIELD OF THE INVENTION

The present invention relates to treatment regimens for inflammatory bowel disease comprising administration of long acting dosage forms of a pharmaceutically acceptable salt of glatiramer in combination with adipose-derived stem cells.

BACKGROUND OF THE INVENTION

Inflammatory bowel disease (IBD) is a generic classification which includes several forms of inflammatory diseases and conditions affecting various parts of the gastrointestinal (GI) tract, such as the colon and small intestine. The main forms of IBD include Crohn's disease and ulcerative colitis, among other forms of colitis. An improper activation of the intestinal immune system involving mainly CD4 Th1 cells and an imbalance between pro-inflammatory and anti-inflammatory reactivity play a pivotal role in the pathogenesis of IBD (Shanahan (2001) *Gastroenterology* 120:622-635). Patients may suffer from diarrhea, nausea, vomiting, abdominal cramps, and uncontrolled pain. The most commonly used conventional therapies are anti-inflammatory medicaments such as corticosteroids, and immunosuppressives. Current therapies for IBD are systemic administration of anti-inflammatory drugs such as corticosteroids, and immunosuppressives or surgery, which are only partially effective, have serious side effects, cause morbidity and do not cure the disease.

Aharoni et al. ((2006) *JPET*, 318:68-78) investigated the effect of the immunomodulator glatiramer acetate (also known as Copolymer 1, marketed under the tradename Copaxone®) on two murine models of IBD, chemically induced and spontaneous.

U.S. Pat. No. 8,008,258 discloses the use of Copolymer 1, or a Copolymer 1-related peptide, for the treatment of inflammatory bowel disease such as Crohn's disease and ulcerative colitis, by daily administration. Copolymer-1 was administered orally or parenterally by daily subcutaneous injections.

Copolymer-1/glatiramer acetate is a random polymer composed of the four amino acids L-glutamic acid, L-alanine, L-tyrosine and L-lysine that are found in myelin basic protein. The average molar fractions of the amino acids are 0.141, 0.427, 0.095 and 0.338, respectively, and the average molecular weight of copolymer-1 is between 4,700 and 11,000 daltons. Chemically, glatiramer acetate is designated L-glutamic acid polymer with L-alanine, L-lysine and L-tyrosine, acetate (salt). Its structural formula is: (Glu, Ala, Lys, Tyr)$_x$CH$_3$COOH or (C$_5$H$_9$NO$_4$_S$_3$H$_7$NO$_2$_C$_6$H$_{14}$N$_2$O$_2$_C$_9$H$_{11}$NO$_3$)xC$_2$H$_4$O$_2$ [CAS-147245-92-9], approx. ratio Glu$_{14}$Ala$_{43}$Tyr$_{10}$Lyz$_{34}$x (CH$_3$COOH)$_{20}$. Copaxone® is a clear, colorless to slightly yellow, sterile, non-pyrogenic solution for subcutaneous injection. Each milliliter contains 20 mg of glatiramer acetate and 40 mg of mannitol. The pH range of the solution is approximately 5.5 to 7.0. Copaxone® is indicated for the treatment of patients with relapsing forms of multiple sclerosis.

The mechanism of action for glatiramer acetate is unknown, although some important immunological properties of this copolymer have emerged. Administration of glatiramer acetate shifts the population of T cells from pro-inflammatory Th1 cells to regulatory Th2 cells that suppress the inflammatory response (FDA Copaxone® label). Given its resemblance to myelin basic protein, glatiramer acetate may also act as a decoy, diverting an autoimmune response against myelin. The integrity of the blood-brain barrier, however, is not appreciably affected by glatiramer acetate, at least not in the early stages of treatment. Glatiramer acetate has been demonstrated to be active when injected subcutaneously, intraperitoneally, intravenously or intramuscularly (Teitelbaum et al., (1971) *Eur J Immunol*, 1 242-248; Teitelbaum et al., (1973) *Eur J Immunol*, 3 273-279).

U.S. Pat. No. 8,377,885 discloses long acting parenteral pharmaceutical compositions comprising a therapeutically effective amount of glatiramer, and in particular, a composition comprising a therapeutically effective amount of glatiramer acetate in depot form suitable for subcutaneous or intramuscular implantation or injection in treating multiple sclerosis.

U.S. Pat. No. 8,796,226 discloses depot compositions comprising glatiramer acetate and at least one additional drug.

Mesenchymal stem cells or marrow stromal cells (MSCs) are adult multipotent stem cells that were originally identified in the bone marrow stroma, where they regulate key stages of haematopoiesis. There have since been many claims that they also exist in a wide variety of other tissues. MSCs can be expanded in vitro and, under appropriate conditions, can give rise to several cell types, including bone and fat precursors. The in vitro-expanded cells have remarkable immunoregulatory properties and effects on tissue repair; because of this, their potential use as therapeutic agents in vivo is being extensively studied.

It has been shown over the past few decades that adipose tissue is in addition to its main function as an energy reservoir also an abundant resource for multipotent stromal cells (Zuk et al., 2002, *Mol Biol Cell*, 13: 4279-4295). Adipose tissue as a source for multipotent stromal/stem cells has several advantages over other sources (Baer et al., 2012, *Stem Cells Int;* 2012: 812693). For example, subcutaneous adipose depots are ubiquitous and easily accessible in large quantities with a minimal invasive procedure, namely, liposuction aspiration. The lipoaspirate is typically discarded as medical waste, qualifying this starting material as a good source of adipose-derived mesenchymal stromal/stem cells (ASCs) for further cell isolation.

Flores et al., (2015) *World J Stem Cells*, 7(2): 343-351, and Chinnadurai et al., (2015) *World J Gastroenterol*, 21(16): 4779-4787) review preclinical and clinical studies on stem cell therapy in inflammatory bowel disease. Flores et al. note that although cell therapies are promising candidates for the treatment of IBD, inconsistent results have emerged from clinical trials using hematopoietic stem cells (HSCs) and mesenchymal stem cells (MSCs), and that up to now the results are unpredictable. In order to develop an effective therapy, in-depth basic research is necessary. Chinnadurai et al. note that the results proved MSC therapy is safe but efficacy data remains elusive and conflicting clinical benefit has been reported so far.

WO 2010/045645 discloses methods of recovering adipose stem cells from adipose tissue.

U.S. Pat. No. 8,021,882 discloses a method for producing stem cell conditioned media for treatment of neurological insults, by providing a culture of adipose stem cells and collecting the supernatants thereof.

Adipose-derived stem cells are being tested for the treatment of perianal fistulising Crohn's disease (Panés et al., 2016, *Gastroenterology*, 150 (4): S181).

There is still a need in the art for novel therapies for IBD and related disorders that are safe, long acting and which enable a significant improvement in the quality of life of the patients.

SUMMARY OF THE INVENTION

The present invention provides according to some aspects combined therapies for inflammatory bowel disease (IBD) using long acting parenteral pharmaceutical compositions comprising a pharmaceutically acceptable salt of glatiramer, the compositions being in a sustained release depot form, and adipose-derived stem cells. In particular embodiments, methods of treating IBD are provided, which comprise parenteral administration or implantation of a composition comprising a therapeutically effective amount of glatiramer acetate in depot form, and administration of adipose-derived stem cells.

The present invention is based in part on the surprising synergistic effect of a combination of glatiramer acetate depot (GA Depot) and human adipose-derived stem cells (ADSCs) demonstrated in a mouse model of IBD as exemplified herein below. It was surprisingly found that the combined treatment significantly reduced the severity of, and in some cases even prevented, IBD manifestations, including rectal bleeding and shortening of the colon. The combined treatment also decreased colon histological score and Daily Activity Index, which is a combined measurement of weight change, stool consistency and bleeding. This is in contrast to each treatment alone, which only showed a limited insignificant effect on the disease manifestations.

According to one aspect, the present invention provides a method of treating inflammatory bowel disease comprising administering to a subject in need thereof a pharmaceutical composition comprising glatiramer acetate, the pharmaceutical composition being in a sustained release depot form, and administering human adipose-derived stem cells (hADSCs).

According to some embodiments, the pharmaceutical composition comprising glatiramer acetate and the hADSCs are administered on the same day. According to other embodiments, the pharmaceutical composition comprising glatiramer acetate and the hADSCs are administered on separate days.

According to some embodiments, a period of time between administration of the pharmaceutical composition comprising glatiramer acetate and administration of the hADSCs ranges between 1-14 days. According to additional embodiments, a period of time between administration of the pharmaceutical composition comprising glatiramer acetate and administration of the hADSCs ranges between 1-2 weeks.

According to some embodiments, the pharmaceutical composition comprising glatiramer acetate is administered once every 1-15 weeks. According to additional embodiments, the pharmaceutical composition comprising glatiramer acetate is administered once every 1-10 weeks. According to yet additional embodiments, the pharmaceutical composition comprising glatiramer acetate is administered once every 1-6 weeks, for example once every 2-6 weeks. According to some specific embodiments, the pharmaceutical composition comprising glatiramer acetate is administered once every 4 weeks.

According to some embodiments, the hADSCs are administered once.

According to other embodiments, the hADSCs are administered more than once, for example twice, three times, four times, etc. Each possibility represents a separate embodiment of the present invention. According to some embodiments, the hADSCS are administered once every 2-8 months. According to additional embodiments, the hADSCs are administered once every 3-12 months.

According to some embodiments, the pharmaceutical composition comprising glatiramer acetate is administered first, before administration of the hADSCs. According to other embodiments, the pharmaceutical composition comprising glatiramer acetate is administered second, after administration of the hADSCs.

According to some embodiments, the pharmaceutical composition comprising glatiramer acetate is formulated for intramuscular administration, and the administering is via intramuscular injection According to other embodiments, the pharmaceutical composition comprising glatiramer acetate is formulated for subcutaneous implantation, and the administering is via subcutaneous injection.

According to some embodiments, administering the hADSCs is via systemic administration. According to some embodiments, the systemic administration is selected from the group consisting of intraperitoneal, intravenous and intramuscular injections. Each possibility represents a separate embodiment of the present invention.

According to other embodiments, administering the hADSCs is via local administration. In some specific embodiment, the local administration is into an enteric lesion of the subject or into a perianal fistula. Each possibility represents a separate embodiment of the present invention.

The hADSCs may be obtained by liposuction procedures in various areas of the body including stomach, hips, thighs, arms, neck and buttocks. According to some embodiments, the hADSCs are derived from human subcutaneous fat obtained by liposuction aspiration.

According to some embodiments, the hADSCs are autologous.

According to other embodiments the hADSCs are allogeneic.

According to some embodiments, the hADSCs are characterized by positive expression of CD44, CD73 and CD90 by at least 95% of the cells, positive expression of CD105 by at least 90% of the cells, and negative expression of CD45, CD19, CD11B and HLADR by at least 95% of the cells. According to some embodiments, the hADSCs are further characterized by positive expression of CD34 by 0.1-10% of the cells.

According to some embodiments, administering the hADSCs comprises administrating about $10^5$-$5\times10^8$ cells per one administration. According to some embodiments, administering the hADSCs comprises administrating about $50\times10^6$-$500\times10^6$.

According to some embodiments, the glatiramer acetate comprises the acetate salt of L-alanine, L-glutamic acid, L-lysine, and L-tyrosine in the molar ratios of about 0.14 glutamic acid, about 0.43 alanine, about 0.10 tyrosine and about 0.33 lysine.

According to some embodiments, the glatiramer acetate comprises about 15 to about 100 amino acids.

According to some embodiments, the pharmaceutical composition comprising glatiramer acetate comprises 20 to 500 mg of glatiramer acetate. According to additional embodiments, the pharmaceutical composition comprising glatiramer acetate comprises 20 to 250 mg of glatiramer acetate. According to yet additional embodiments, the pharmaceutical composition comprising glatiramer acetate comprises 20 to 100 mg of glatiramer acetate.

According to some embodiments, the pharmaceutical composition comprising glatiramer acetate further comprises a pharmaceutically acceptable biodegradable or non-biodegradable carrier.

According to some embodiments, the carrier is selected from the group consisting of poly (D,L-lactide-co-glycolide) (PLGA), poly (D,L-lactide) (PLA), polyglycolides (PGA), polycaprolactone, polyhydroxybutyrate, polyorthoesters, polyalkaneanhydrides, gelatin, collagen, oxidized cellulose, and polyphosphazene. Each possibility represents a separate embodiment of the invention.

According to some embodiments, the pharmaceutical composition comprising glatiramer acetate is in the form of microparticles prepared by a water-in oil-in water double emulsification process.

According to some embodiments, the pharmaceutical composition comprising glatiramer acetate comprises an internal aqueous phase comprising a therapeutically effective amount of glatiramer acetate, a water immiscible polymeric phase comprising a carrier selected from a biodegradable and a non-biodegradable polymer, and an external aqueous phase. In some specific embodiments, the water immiscible polymeric phase comprises a biodegradable polymer selected from PLA and PLGA. Each possibility represents a separate embodiment of the invention. In additional specific embodiments, the external aqueous phase comprises a surfactant selected from polyvinyl alcohol (PVA), polysorbate, polyethylene oxide-polypropylene oxide block copolymers and cellulose esters. Each possibility represents a separate embodiment of the invention.

The present invention encompasses a pharmaceutical composition comprising glatiramer acetate, the pharmaceutical composition being in a sustained release depot form, for use with hADSCs in the treatment of inflammatory bowel disease.

The present invention further encompasses the use of glatiramer acetate in sustained-release depot form suitable for administration or implantation to/into a subject in need thereof, for the manufacture of a medicament for use with hADSCs in the treatment of inflammatory bowel disease.

The present invention also encompasses the combination of glatiramer acetate in a depot form and hADSCs, with at least one additional drug for the treatment of inflammatory bowel disease.

According to some embodiments, the inflammatory bowel disease is selected from the group consisting of Crohn's disease, ulcerative colitis, granulomatous colitis, lymphocyte colitis, collagenous colitis, diversion colitis and coeliac disease. Each possibility represents a separate embodiment of the present invention. In some specific embodiments, the inflammatory bowel disease is Crohn's disease. In additional specific embodiments, the inflammatory bowel disease is ulcerative colitis.

The subject to be treated as described herein is typically a human.

These and further aspects and features of the present invention will become apparent from the detailed description, examples and claims which follow.

DETAILED DESCRIPTION OF THE INVENTION

The present invention is directed to treatment methods for inflammatory bowel disease comprising administration of sustained-release, long acting dosage forms of a pharmaceutically acceptable salt of glatiramer in combination with adipose-derived stem cells. The present invention is based in part on the surprising synergistic effect of a combination of glatiramer acetate depot (GA Depot) and human adipose-derived stem cells (hADSCs) on clinical manifestations in an animal model of IBD.

Encompassed by the present invention is a combination therapy of glatiramer acetate or any other pharmaceutically acceptable salt of glatiramer with adipose-derived stem cells and optionally at least one other active agent.

The term "treating" as used herein with respect to inflammatory bowel disease refers to alleviating, suppressing, preventing, delaying the onset and/or attenuating the progression of the disease or at least one symptom thereof after the onset of the disease. Common symptoms after the onset of inflammatory bowel disease include, but are not limited to, diarrhea, abdominal pain and cramping, blood in the stool, ulcer colon shortening, and/or histomorphological changes, as well as reduced appetite and weight loss. According to some embodiments, treating encompasses reduction or even prevention of inflammatory relapses associated with IBD.

The "subject" to which the treatments are administered is a mammal, typically, a human.

According to some embodiments, the inflammatory bowel disease is selected from the group consisting of Crohn's disease, granulomatous colitis, lymphocyte colitis, collagenous colitis, ulcrerative colitis, diversion colitis and coeliac disease. Each possibility represents a separate embodiment of the invention.

The combination therapy according to the present invention may be administered to the subject simultaneously or sequentially in any order at a time interval determined by a skilled artisan. According to some embodiments, the ADSCs and glatiramer acetate composition are administered according to an alternating schedule.

According to some embodiments, the glatiramer acetate composition is administered every 2-6 weeks. According to some embodiments, the glatiramer acetate composition is administered every 4 weeks.

According to some embodiments, the ADSCs are administered once. According to some embodiments, the ADSCs are administered multiple times, for example every 2-8 months, every 3-12 months, or less frequent.

According to some embodiments, the ADSCs are administered once and the glatiramer acetate composition is administered once every 2-6 weeks, for example once every 4 weeks.

Adipose-Derived Stem Cells

The present invention utilizes adipose-derived mesenchymal stem cells. As used herein, the terms "adipose-derived mesenchymal stem cells" or "adipose-derived stem cells", abbreviated "ADSCs" or "hADSCs" (i.e., human adipose-derived stem cells), refer to plastic-adherent, multipotent cell population harvested from adipose tissue. The cell population is characterized by positive expression of CD44, CD73 and CD90 by at least 95% of the cells, positive expression of CD105 by at least 90% of the cells, and negative expression of CD45, CD19, CD11B and HLADR by at least 95% of the cells.

In some embodiments, the cell population is characterized by positive expression of CD44, CD73 and CD90 by at least 98% of the cells, positive expression of CD105 by at least 90% of the cells, and negative expression of CD45, CD19, CD11B and HLADR by at least 98% of the cells.

The cell population is further characterized by positive expression of CD34 by up to 10%-20% of the cells. In some embodiments, the cell population is characterized by positive expression of CD34 by up to 5%, 6%, 7%, 8%, 9% or 10% of the cells. Each possibility represents a separate embodiment of the present invention.

In some embodiments, at least about 50% of the human ADSCs are positive for CD105, CD73, CD44 and CD90 and negative for CD45, CD19, CD11B, and HLADR.

According to some embodiments, about 90-100% of the hADSCs are positive for the markers: CD44, CD73 and CD90. According to additional embodiments, at least about 95% of the hADSCs are positive for the markers: CD44, CD73 and CD90. According to yet additional embodiments, at least about 98% of the hADSCs are positive for the markers: CD44, CD73 and CD90.

According to some embodiments, about 65-100% of the hADSCs are positive for CD105. According to additional embodiments, about 80-100%, for example 80-95% of the hADSCs are positive for CD105. According to yet additional embodiments, about 90-100% of the hADSCs are positive for CD105.

According to some embodiments, up to about 30% of the hADSCs are positive for CD34.

According to some embodiments, about 0.1-20% of the hADSCs are positive for CD34. According to additional embodiments, about 0.1-10% of the human ADSCs are positive for CD34. According to yet additional embodiments, about 0.3-10% of the hADSCs are positive for CD34, for example about 2-10%. Each possibility represents a separate embodiment of the invention. According to yet additional embodiments, about 0.1-5% of the human ADSCs are positive for CD34. According to yet additional embodiments, about 0.5-2% of the human ADSCs are positive for CD34.

According to some embodiments, at least about 90% of the administered human ADSCs are negative for the markers: CD45, CD19, CD11B and HLADR. According to some embodiments at least about 95% of the hADSCs are negative for the markers: CD45, CD19, CD11B and HLADR. According to yet additional embodiments, at least about 98% of the administered human ADSCs are negative for the markers: CD45, CD19, CD11B and HLADR.

According to some embodiments, at least about 50% of the hADSCs are positive for CD105, CD73, CD44 and CD90 and negative for CD45, CD19, CD11B, and HLADR.

According to additional embodiments, at least about 60%, about 70%, about 80% or about 90% of the hADSCs are positive for CD105, CD73, CD44 and CD90 and negative for CD45, CD19, CD11B, and HLADR. Each possibility represents a separate embodiment of the invention.

Characterization of cell surface marker expression can be performed by methods known in the art, for example using fluorescence-activated cell sorting (FACS). FACS protocols are reviewed, for example, in: Flow Cytometry Protocols, Methods in Molecular Biology Volume 699 2011, Editors: Teresa S. Hawley, Robert G. Hawley Humana Press. Exemplary procedures are described below.

According to some embodiments, the hADSCs are derived from human subcutaneous fat obtained by liposuction aspiration. The hADSCs may be obtained by liposuction procedures in various areas of the body including stomach, hips, thighs, arms, neck and buttocks.

Any procedure of liposuction may be used according to the present invention for obtaining hADSCs, including but not limited to laser, ultrasound and fat removal by abdominoplasty, as known in the art.

The subcutaneous fat is processed to isolate the adipose-derived stem cells, for example according to the procedure described in Example 1 below. Preparation methods typically include steps of washing the tissue with buffers such as PBS and saline, and/or with growth media such as DMEM, StemMACS™ or Plasma-Lyte, and treating the tissue with a tissue-dissociation enzyme such as collagenase and/or subjecting the tissue to mechanical agitation/disruption. Digestion of the sample can also be performed using a combination of dispase and collagenase. Liposomes, which are generally aggregated, can be separated from free stromal cells which include the stem cells and other cells such as red blood cells endothelial cells, and fibroblast cells, by centrifugation. Erythrocytes can be lysed from the suspended pellet using a suitable lysis buffer and the remaining cells can be filtered or centrifuged.

Optionally, cells may be separated by cell sorting or separated immunohistochemically. Bunnell et al. (2008) *Methods.*, 45(2): 115-120, review methods for isolation of ADSCs.

In some preferred embodiments, the ADSCs are cultured before being provided to a subject in need thereof (or before being stored for later use). Preferably, the cells are cultured in a xeno-free medium. In some embodiments, the ADSCs are grown to about 80-100% confluency, for example to about 80% confluency, and sub-cultured to a passage number between 3-10, preferably between 3-5, or 3-4, before administration to the subject. Thus, in some embodiments, the administered cells are at a passage between 3 to 5. In some embodiments, the ADSCs are sub-cultured to passage number 3. In some embodiments, the ADSCs are sub-cultured to passage number 4. In some embodiments, the ADSCs are sub-cultured to passage number 5.

Before administration, cells are counted and prepared for injection in a pharmaceutically acceptable diluent/carrier. Typically, the cells are concentrated before administration to the subject. The concentration typically ranges from $1.6 \times 10^4$ cells/ml to $100 \times 10^6$ cells/ml.

According to some embodiment, administering the hADSCs comprises administering $10^5$-$5 \times 10^8$ cells per one administration. According to some embodiments, administering the hADSCs comprises administering $10^5$-$3 \times 10^8$ cells per one administration. According to additional embodiments, administering the hADSCs comprises administering $50 \times 10^6$-$500 \times 10^6$ cells per one administration. According to yet additional embodiments, administering the hADSCs comprises administering $50 \times 10^6$-$300 \times 10^6$ cells per one administration. According to yet additional embodiments, administering the hADSCs comprises administrating about $10^5$-$10^8$ per one administration, for example about $10^6$-$10^7$ cells per one administration.

As used herein, the term "about", when referring to a measurable value is meant to encompass variations of +/−10%, preferably +/−5%, more preferably +/−1%, and still more preferably +/−0.1% from the specified value.

A composition comprising the ADSCs may be administered systemically by parenteral administration, for example via a route of administration selected from intraperitoneal, intravenous injection and intramuscular injections, as known in the art. Each possibility represents a separate embodiment of the present invention.

Alternatively, a composition comprising the ADSCs may be administered locally, for example into an enteric lesion of the treated subject. Local administration may also be into a perianal fistula. Each possibility represents a separate embodiment of the present invention.

Glatiramer Depot Formulations

The present invention utilizes long acting pharmaceutical compositions comprising a therapeutically effective amount of glatiramer acetate or any other pharmaceutically acceptable salt of glatiramer in a depot form suitable for parenteral administration at a medically acceptable location in a subject in need thereof.

The term "glatiramer acetate" as used herein refers to a compound formerly known as Copolymer 1 that is sold under the trade name Copaxone® and consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate in Copaxone® is 4,700-11,000 daltons (FDA Copaxone® label) and the number of amino acid ranges between about 15 to about 100 amino acids. The term also refers to chemical derivatives and analogues of the compound. Typically, the compound is prepared and characterized as specified in any of U.S. Pat. Nos. 5,981,589; 6,054,430; 6,342,476; 6,362,161; 6,620,847; and 6,939,539.

The term "parenteral" refers according to some embodiments to routes selected from subcutaneous (SC), intravenous (IV), intramuscular (IM), intradermal (ID), and intraperitoneal (IP). Each possibility represents a separate embodiment of the invention.

In some embodiments, the glatiramer formulation is administered by intramuscular, subcutaneous, percutaneous, intravenous, or inhalation administration. Each possibility represents a separate embodiment of the invention. According to certain specific embodiments, the glatiramer formulation is for subcutaneous or intramuscular implantation.

The term "therapeutically effective amount" as used herein is intended to qualify the amount of the copolymer that will achieve the goal of alleviation of the symptoms of IBD. Suitable doses include, but are not limited to, 20-750 mg for each dosage form. However, it is understood that the amount of the copolymer administered will be determined by a physician, according to various parameters including the chosen route of administration, the age, weight, and the severity of the patient's symptoms. According to various embodiments of the present invention, the therapeutically effective amount of the at least one copolymer ranges from about 1 mg to about 500 mg/day. Alternatively, such therapeutically effective amounts of the at least one copolymer are from about 20 mg to about 100 mg/day.

The term "sustained-release depot form" and "long acting" refers to a composition which provides prolonged or extended release of the glatiramer salt to the systemic circulation of a subject or to local sites of action in a subject. In particular, the long acting, sustained-release pharmaceutical compositions of the present invention provide a dosing regimen which ranges from once weekly to once every 6 months. According to some embodiments, the dosing regimen ranges from once a week, twice monthly (approximately once in every 2 weeks) to once monthly. Depending on the duration of action required, each depot or implantable device of the present invention will typically contain between about 20 and 750 mg of the active ingredient, designed to be released over a period of time ranging from a couple of weeks to a number of months. According to some embodiments, the pharmaceutical composition comprising glatiramer acetate is suitable for a dosing schedule from once weekly to once in every 6 months. According to particular embodiments, the composition is suitable for dosing from once every 2 weeks to once monthly.

According to some embodiments, the pharmaceutical composition comprising glatiramer acetate is in the form of biodegradable microspheres, non-biodegradable microspheres, implants of any suitable geometric shape, including implantable rods, implantable capsules, implantable rings, or prolonged release gels or erodible matrices.

In some embodiments, the depot formulations used in the methods of the present invention include, but are not limited to, suspensions of glatiramer or a pharmaceutically acceptable salt thereof in water, oil or wax phase; poorly soluble polyelectrolyte complexes of glatiramer or a pharmaceutically acceptable salt thereof; "in-situ" gel-forming matrices based on the combination of water-miscible solvent with glatiramer or a pharmaceutically acceptable salt thereof; and biodegradable polymeric microparticles with incorporated glatiramer or a pharmaceutically acceptable salt thereof. Each possibility represents a separate embodiment of the invention. In particular, the compositions of the present invention are in the form of injectable microparticles wherein the glatiramer or pharmaceutically acceptable salt thereof is entrapped in a biodegradable or non-biodegradable carrier. The microparticulate compositions of the present invention may comprise a water-in oil-in water double emulsion. Within the scope of the present invention is a microparticulate composition comprising an internal aqueous phase comprising glatiramer or any pharmaceutically acceptable salt thereof, an oil phase or water-immiscible phase comprising a biodegradable or non-biodegradable polymer and an external aqueous phase. The external aqueous phase may further comprise a surfactant, for example, polyvinyl alcohol (PVA), polysorbate, polyethylene oxide-polypropylene oxide block copolymers or cellulose esters. The terms "oil phase" and "water-immiscible phase" may be used interchangeably herein.

In some embodiments, the composition may comprise any other pharmaceutically acceptable salt of glatiramer including, but not limited to, sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, tocopheryl succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-2-sulfonate, p-toluenesulfonate and mandelate. Each possibility represents a separate embodiment of the invention.

The copolymers can be made by any procedure available to one of skill in the art. For example, the copolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example, dicyclohexylcarbodiimide, can be used to facilitate the formation of the peptide bond.

Blocking groups can be used to protect functional groups, such as the side chain moieties and some of the amino or carboxyl groups against undesired side reactions. The process disclosed in U.S. Pat. No. 3,849,550 can be used for preparing the copolymers of the invention. For example, the N-carboxyanhydrides of tyrosine, alanine, γ-benzyl glutamate and N, ε-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by one molar piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine. U.S. Pat. Nos. 6,620,847; 6,362,161; 6,342,476; 6,054,430; 6,048,898 and 5,981,589 disclose improved methods for preparing glatiramer acetate (Cop-1). For purposes of this application, the terms "ambient temperature" and "room temperature" typically means a temperature ranging from about 20° C. to about 26° C.

Long-acting depot formulations of GA are disclosed for example in U.S. Pat. No. 8,377,885. In a non-limiting example, GA Depot is an aseptic lyophilized powder comprising Polyglactin microparticles loaded with GA. This formulation is suspended in water for injection and is intended for intra-muscular administration once every 4 weeks for example.

The molecular weight of the copolymers can be adjusted during polypeptide synthesis or after the polymers have been made. To adjust the molecular weight during polypeptide synthesis, the synthetic conditions or the amounts of amino acids are adjusted so that synthesis stops when the polypeptide reaches the approximate desired length. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the copolymers with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by the test reaction. The trifluoroacetyl-polypeptide with the desired molecular weight profile is then further treated with an aqueous piperidine solution to form a deprotected polypeptide having the desired molecular weight.

In a preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

In certain embodiments, the dosage forms include, but are not limited to, biodegradable injectable depot systems such as, PLGA based injectable depot systems; non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as poly(e-caprolactone) i.e. PCL (Lactel® from Durect); polyanhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly(p-{carboxyphenoxy}methane), CPM; poly(p-{carboxyphenoxy}propane), CPP; poly(p-{carboxyphenoxy}hexane) s CPH; polyamines, polyurethanes, polyesteramides, polyorthoesters {CHDM: cis/trans-cyclohexyl dimethanol, HD: 1,6-hexanediol. DETOU: (3,9-diethylidene-2,4,8,10-tetraoxaspiro undecanc)}; polydioxanones; polyhydroxybutyrates; polyalkylene oxalates; polyamides; polyesteramides; polyurethanes;

polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) triblock copolymers (PEO—PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof.

In some embodiments, the compositions of the present invention comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphosphazene and the like. Each possibility represents a separate embodiment.

In some specific embodiments, the biodegradable polymer is a lactic acid-based polymer, for example polylactide, or poly (D, L-lactide-co-glycolide) i.e. PLGA. In some embodiment, the biodegradable polymer is present in an amount between about 10% to about 98% w/w of the composition. The lactic acid-based polymer has a monomer ratio of lactic acid to glycolic acid in the range of 100:0 to about 0:100, for example, 100:0 to about 10:90 and has an average molecular weight of from about 1,000 to 200,000 daltons. However, it is understood that the amount of biodegradable polymer is determined by parameters such as the duration of use and the like.

The compositions of the present invention may further comprise one or more pharmaceutically acceptable excipient(s) selected from, but not limited to, co-surfactants, solvents/co-solvents, water immiscible solvents, water, water miscible solvents, oily components, hydrophilic solvents, emulsifiers, preservatives, antioxidants, anti-foaming agents, stabilizers, buffering agents, pH adjusting agents, osmotic agents, channel forming agents, osmotic adjustment agents, or any other excipient known in the art. Suitable co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Each possibility represents a separate embodiment of the invention. Suitable solvents/co-solvents include, but not limited to, alcohols, triacetin, dimethyl isosorbide, glycofurol, propylene carbonate, water, dimethyl acetamide, and the like or mixtures thereof. Each possibility represents a separate embodiment of the invention. Suitable anti-foaming agents include, but are not limited to, silicon emulsions or sorbitan sesquioleate. Suitable stabilizers to prevent or reduce the deterioration of the components in the compositions of the present invention include, but are not limited to, antioxidants such as glycine, α-tocopherol or ascorbate, BHA, BHT, and the like or mixtures thereof. Each possibility represents a separate embodiment of the invention. Suitable tonicity modifiers include, but are not limited to, mannitol, sodium chloride, and glucose. Each possibility represents a separate embodiment of the invention. Suitable buffering agents include, but are not limited to, acetates, phosphates, and citrates with suitable cations. Each possibility represents a separate embodiment of the invention.

The compositions of the present invention can be prepared by any manner known in the art, for example, by incorporation of the glatiramer or salt thereof copolymer into a colloidal delivery system, e.g., biodegradable microparticles, thus allowing release retardation by diffusion through polymeric walls of the particle and by polymer degradation in water media or biological fluids in the body. The compositions of the present invention can be prepared in the form of injectable microparticles by a process known as the "double emulsification". Briefly, the concentrated solution of the water-soluble copolymer is dispersed in a solution of the biodegradable or non-biodegradable polymer in water-immiscible volatile organic solvent (e.g. methylene chloride, chloroform and the like). The thus obtained "water-in-oil" (w/o) emulsion is then dispersed in a continuous external water phase containing surfactant (e.g. polyvinyl alcohol—PVA, polysorbates, polyethylene oxide-polypropylene oxide block copolymers, cellulose esters and the like) to form "water-in oil-in water (w/o/w) double emulsion" droplets. After evaporation of the organic solvent, the microparticles solidify and are collected by filtration or centrifugation. The collected microparticles (MPs) are washed with purified water to eliminate most of the surfactant and non-bonded peptide and centrifugated again. The washed MPs are collected and lyophilized without additives or with the addition of cryoprotectant (mannitol) to facilitate their subsequent reconstitution.

The particle size of the "water-in oil-in water (w/o/w) double emulsion" can be determined by various parameters including, but not limited to, the amount of applied force at this step, the speed of mixing, surfactant type and concentration, etc. Suitable particle sizes range from about 1 to 100 μm.

The depot systems of the present invention encompass any forms known to a person of skill in the art. Suitable forms include, but are not limited to, biodegradable or non biodegradable microspheres, implantable rods, implantable capsules, and implantable rings. Each possibility represents a separate embodiment of the invention. Further contemplated are prolonged release gel depot and erodible matrices. Each possibility represents a separate embodiment of the invention. Suitable implantable systems are described for example in US 2008/0063687. Implantable rods can be prepared as is known in the art using suitable microextruders such as those described for example in www.randcastle.com/prodinfo.html.

According to the principles of the present invention, the long acting pharmaceutical compositions of the present invention provide equal or superior therapeutic efficacy to the commercially available daily injectable dosage forms, with reduced incidence of side effects and with reduced severity of side effects at the local and/or systemic level. In some embodiments, the compositions of the present invention provide prolonged release or prolonged action of glatiramer in a subject as compared to a substantially similar dose of an immediate release formulation of glatiramer acetate.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1: Effect of Glatiramer Acetate Depot and Human Adipose Derived Stem Cells on DSS-Induced Inflammatory Bowel Disease in Mice Materials and Methods Glatiramer acetate (GA) depot production: GA Depot was prepared as described in U.S. Pat. No. 8,377,885, lyophilized and stored.

Glatiramer acetate (GA) and GA Depot administration: GA (Commercial name Copaxone® 20 mg/ml in pre-filled syringes, Teva Pharmaceutical Industries Ltd., Petah-Tikva, Israel) was injected subcutaneously at 2 mg/mouse/day from day 0 to day 14. GA Depot was suspended in sterile water for injection (WFI) (B Braun, Melsumgen, Germany) and injected intramuscularly (IM) at 10 mg dose (doses of GA Depot are given according to amount of active ingredient, i.e. GA Depot 10 mg contains 10 mg GA) divided to two 5 mg doses on days 0 and 1 due to technical reasons (volume limitation).

Animals: All animal studies were approved by local ethics committees. C57BL/6 female mice, 7-9 weeks old were randomized into control or treatment groups with similar mean weight Animals were given food and water ad libitum throughout the experiment.

Human Adipose Derived Stem Cells (ADSCs) Isolation, Characterization, Culture and Preparation for Injection:

ADSCs isolation: Lipoaspirate derived from human tissue was washed 4 times with an equal volume of PBS at room temperature (RT). The lipoaspirate was then digested with collagenase (NB4, Serva) at 37° C. for 30 minutes with shaking, followed by centrifugation at RT, 300-500 g, for 10 minutes. Subsequently, the upper fluid was removed including undigested fat. The reaction was stopped by adding equal volume of a xeno-free expansion medium (StemMACS™, Miltenyi), followed by an additional centrifugation at RT, 500 g for 10 minutes. The resulting pellet was resuspended in a red blood cells lysis buffer for 10 minutes at RT and the sample centrifuged again. The pellet was resuspended in 10 ml medium and filtered through a 100 μm filter followed by the addition of additional 10 ml of medium. The solution was centrifuged at 500 g for 5 minutes. The same procedure was repeated with a 40 μm filter and the cells were counted. The resulting cells are referred as stromal vascular fraction (SVF).

Cell culture: SVF was plated at a density of ~2×10$^6$ cells per 75 cm$^2$. Cells were grown to ~80% confluency, trypsinized and sub-cultured up to passage 3-4. Cells were then collected and analyzed by FACS for the markers: CD105, CD73, CD90, CD45, CD44, CD19, CD11B, HLADR and CD34. The cells were stored frozen in liquid nitrogen until use. For use, the cells were thawed and plated at a concentration of 50,000 cells/cm$^2$ and incubated overnight. Prior to cells intraperitoneal (IP) injection the cells were trypsinized, counted and prepared for injection at a concentration of 1×10$^6$ cell/100 ul PBS and kept in ice until use for a period no longer than 30 min.

Inflammatory bowel disease (IBD) induction: A widely used IBD model in mice is the dextran sulfate sodium (DSS)-induced colitis. DSS administration in the mice drinking water leads to many of the events presumed to initiate and sustain human IBD (Boismenu and Chen (2000) *J Leukoc Biol*, 67:267-278). This model allows the generation of variable disease forms of acute and chronic nature, depending on the mouse strain or on the dose and frequency of DSS administration. In this example, following randomization into treatment groups of 10 animals each with the same average body weight, acute colitis was induced by giving DSS (mol. wt. 36,000-50,000) (MP Biomedicals, LLC, Eschwege, Germany) in acidified drinking water (1.5% (wt./v)) for 5 days. Naïve mice group (n=3) was not given DSS in the drinking water.

Experimental design: Treatment groups are specified in the following table:

TABLE 1

Treatment groups

| Group | Test article | Diluent | Injection volume/ route | Days of administration |
|---|---|---|---|---|
| DSS only | N/A | N/A | N/A | N/A |
| DSS + Copaxone ® | Copaxone ® 2 mg | N/A | 0.1 mL, SC | 0-14 |
| DSS + GA Depot 10 mg | GA Depot 10mg* | WFI, 0.2 mL | 0.1 mL, IM in each thigh muscle | 0, 1 |
| DSS + ADSCs Day 5 | 1 × 10$^6$ cells | PBS, 0.1 mL | 0.1 mL, IP | 5 |
| DSS + GA Depot 10 mg + ADSCs Day 5 | GA Depot 10 mg* | WFI, 0.2 mL | 0.1 mL, IM in each thigh muscle | 0, 1 |
| | 1 × 10$^6$ cells | PBS, 0.1 mL | 0.1 mL, IP | 5 |
| DSS + ADSCs Day 1 | 1 × 10$^6$ cells | PBS, 0.1 mL | 0.1 mL, IP | 1 |
| DSS + GA Depot 10 mg + ADSCs Day 1 | GA Depot 10 mg* | WFI, 0.2 mL | 0.1 mL, IM in each thigh muscle | 0, 1 |
| | 1 × 10$^6$ cells | PBS, 0.1 mL | 0.1 mL, IP | 1 |
| Naïve | N/A | N/A | N/A | N/A |

*Due to technical considerations, this dose was divided into two 5 mg doses that were administered on days 0 and 1.

Assessment of IBD: Assessment of IBD was performed as previously described (Aharoni et al., (2006) *JPET* 318:68-78). In brief, body weight, rectal bleeding (observation of bleeding signs on the anus or gross bleeding), stool consistency and survival were monitored daily. Hemoccult® test (Beckman Coulter, Inc., Fullerton, Calif.) was used on days 5 and 10.

Daily Disease Activity Index (DAI) was calculated by grading on a scale of 0 to 4 the following parameters: change in weight (0, <1%; 1, 1-5%; 2, 5-10%; 3, 10-15%; and 4, >15%), intestinal bleeding (0, negative; 4, positive), and stool consistency (0, normal; 2, loose stools; 4, diarrhea). The combined scores were then divided by 3 to obtain the final DAI.

Fourteen (14) days following disease induction, mice were sacrificed and the large intestine was collected and evaluated for colon length and microscopic colonic damage. Microscopic scoring was performed for each colon as follows:
 (i) Three transversal samples of 15 mm each were trimmed from the colon: a proximal sample, taken 1 cm from the cecum-colon junction; a middle sample, taken 2 cm distal to the previous; and a distal sample, taken 2 cm distal to the previous. The samples were fixed in 10% phosphate-buffered formalin.
 (ii) Paraffin-embedded sections (5-6 um) were stained with hematoxylin and eosin. The degree of histological damage and inflammation was graded in a blinded fashion by an expert pathologist. The following manifestations were included in the evaluations: the amount of inflammation (0, none; 1, mild; 2, moderate; 3, severe; and 4, accumulation of inflammatory cells in the gut lumen), distribution of lesions (0, none; 1, focal; 2, multifocal; 3, nearly diffuse; and 4, diffuse), depth of inflammation and layers involved (0, none; 1, mucosa only; 2, mucosa and submucosa; 3, limited transmural involvement; and 4, transmural), and nature of mucosal changes (0, none; 2, more degeneration; and 3, more necrosis). The overall histological score is the sum of the four manifestations (maximal score of 15). Reported score for each animal is the mean of scores given for the three sections examined.

Statistical analysis: Each data set was analyzed using single-factor analysis of variance (ANOVA) followed by two-tailed, two-sample students' T test assuming unequal variances, n=10/group, +/−standard error.

| Phenotype of the cells: | |
|---|---|
| Marker (dye) | % expression |
| CD73 (PE*) | 100 |
| CD90 (PE) | 100 |
| CD105 (PE) | 100 |
| CD44 (FITC**) | 100 |
| HLADR (PE) | 0.1 |
| CD34 (PE) | 1.5 |
| CD45 (PE) | 0.5 |
| CD11b (PE) | 0.2 |
| CD19 (PE) | 0.1 |
| IgG1 (PE) | 0.2 |
| IgG2a (PE) | 0.1 |
| IgG1 (FITC) | 0 |

*PE—Phycoerythrin;
**FITC—Fluorescein isothiocyanate

Survival rate: No animals died during the experiment.

Figure 1:
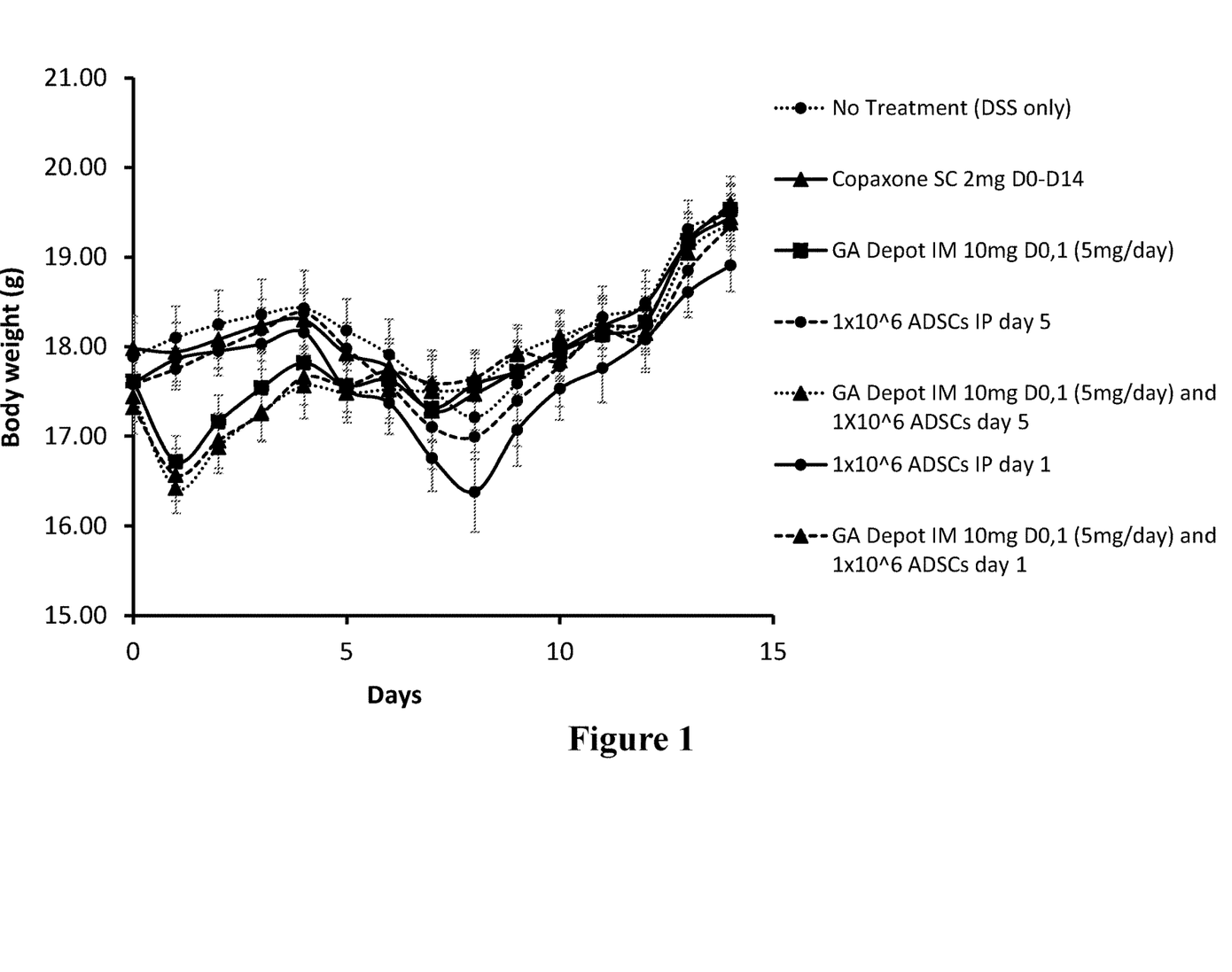
FIG. 1. Effect of GA Depot and ADSCs on DSS-induced IBD as determined by mean body weight. n=10/group, +/−standard error. No scientifically significant differences were noted.

Body weight: The results are summarized in FIG. 1. Mean body weight in the GA Depot+ADSCs groups and in the GA Depot group was lower than all other groups at the disease induction stage (days 0 to 5). From day 5 onwards, mean body weight was similarly elevated in all groups, suggesting improvement in animal condition at all groups including in the no treatment group.

Figure 2:
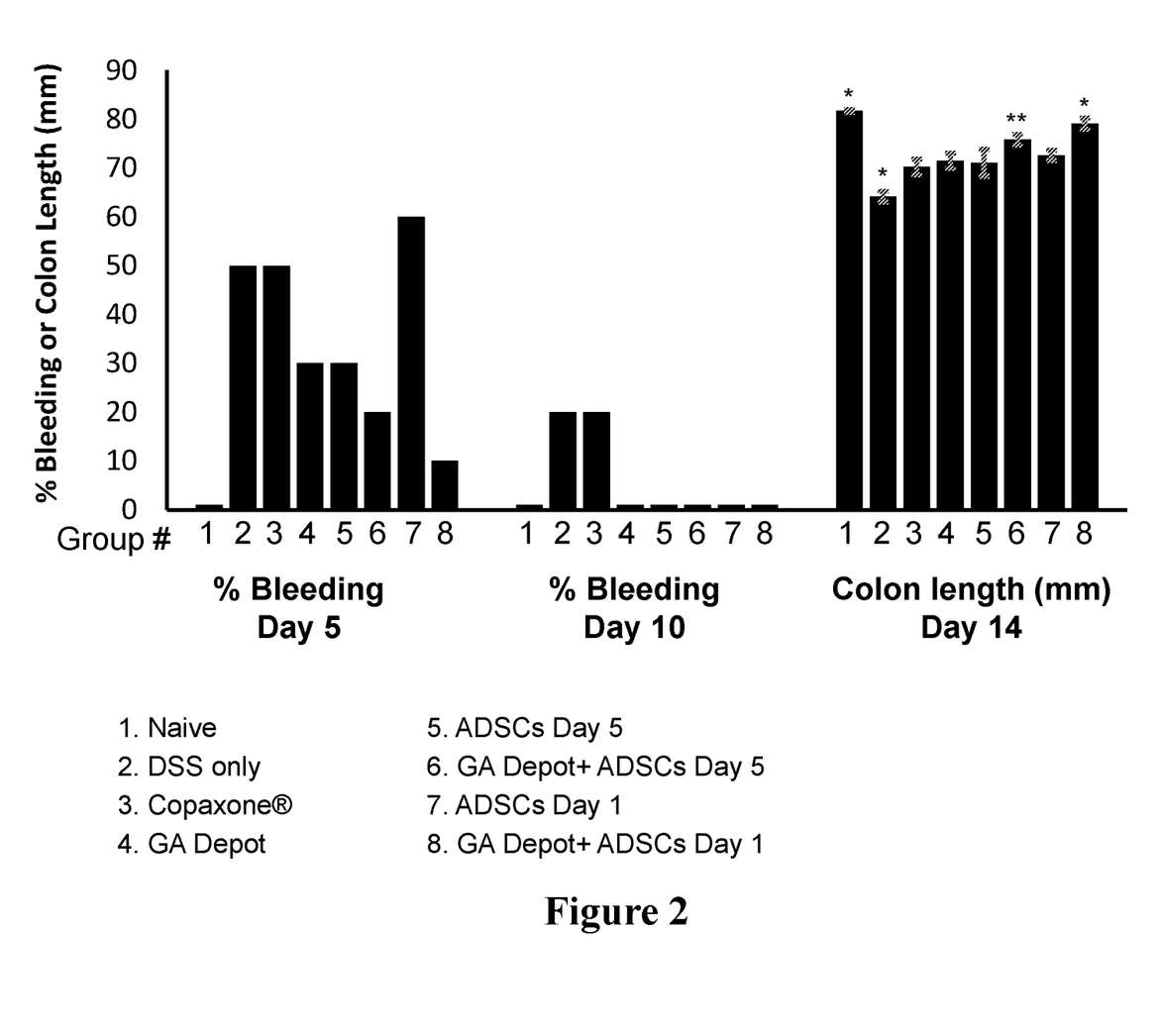
FIG. 2. Effect of GA Depot and ADSCs on DSS-induced IBD as determined by percentage of animals showing rectal bleeding on days 5 and 10, and by colon length on day 14. *$P<0.05$ compared to all groups, **$P<0.05$ compared to all groups except ADSCs Day 5. Single-factor analysis of variance (ANOVA) followed by one-tailed two-sample T test assuming unequal variances, n=10 (3 for naïve group), data presented as mean±standard error.

Bleeding and colon length: The results are summarized in FIG. 2. No bleeding was noted in the naïve group. Bleeding (as observed by Hemoccult® test) was observed in 50% of the animals in the untreated and Copaxone® groups on day 5, and in 20% of the animals of those groups on day 10. The ADSCs Day 5 group and the GA Depot group resulted in 30% bleeding on day 5 and no bleeding on day 10. In the ADSCs Day 1 group, bleeding was observed in 60% of the mice on day 1 and in no animal on day 10. The lowest bleeding rate was noted in the GA Depot+ADSCs Day 1 and GA Depot+ADSCs Day 5 groups (20% and 10% of the mice showed bleeding on day 5, respectively; none showed bleeding on day 10). With respect to colon length, average colon length in the groups treated with GA Depot+ADSCs was higher than all other treatment groups including Copaxone®.

Figure 3:
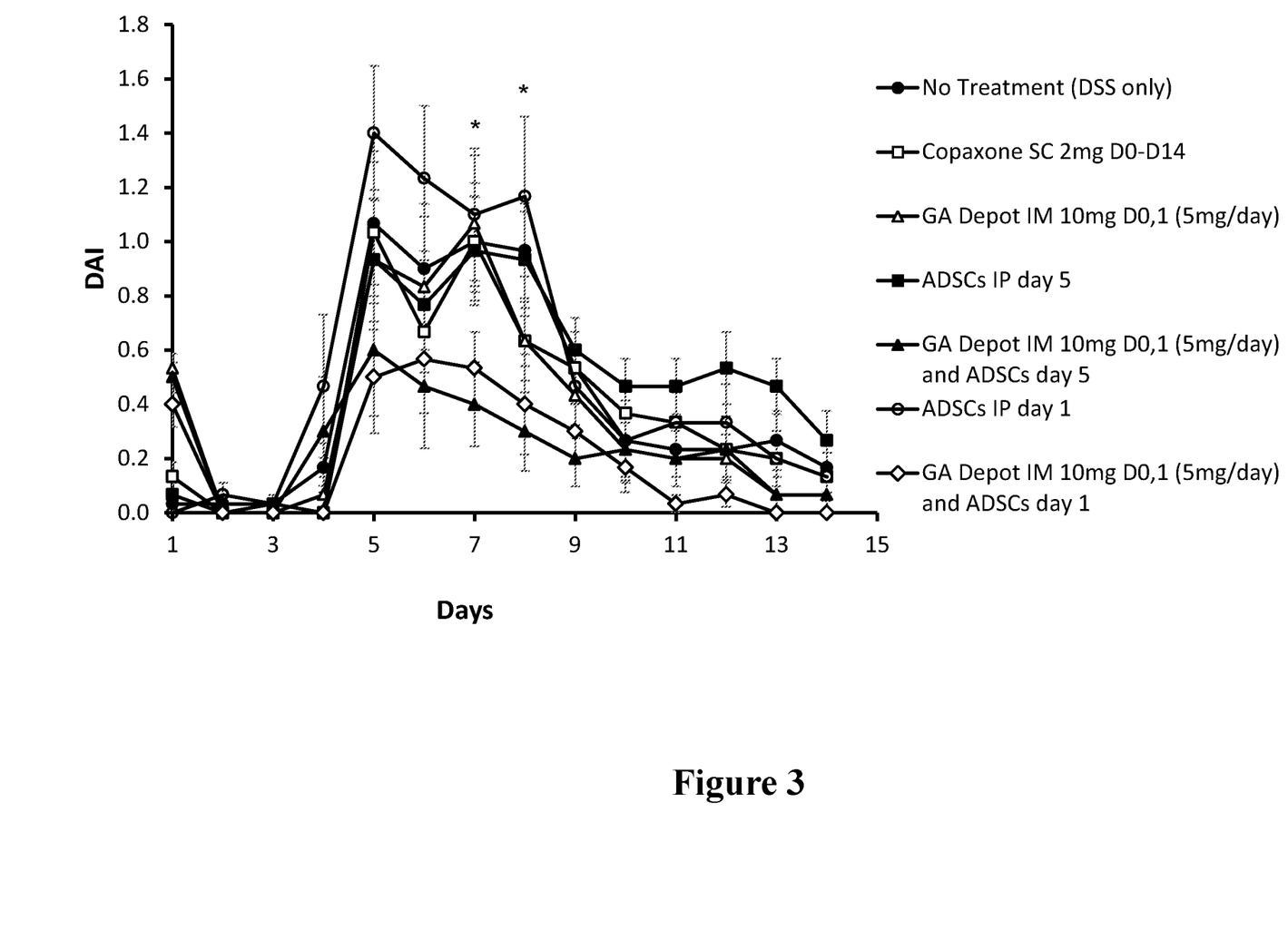
FIG. 3. Effect of GA Depot and ADSCs on DSS-induced IBD as determined by Disease Activity Index (DAI). *$P<0.05$ for GA Depot+ADSCs groups compared to all other groups. Single-factor analysis of variance (ANOVA) followed by one-tailed two-sample T test assuming unequal variances, n=10 (3 for naïve group), data presented as mean±standard error.

Daily Activity Index (DAI): The results are summarized in FIG. 3. The GA Depot+ADSCs groups showed significantly lower DAI values on days 7 and 8 than all other treatment groups including Copaxone®. Overall, disease activity was moderate, with very low DAI from day 11 onwards.

Figure 4:
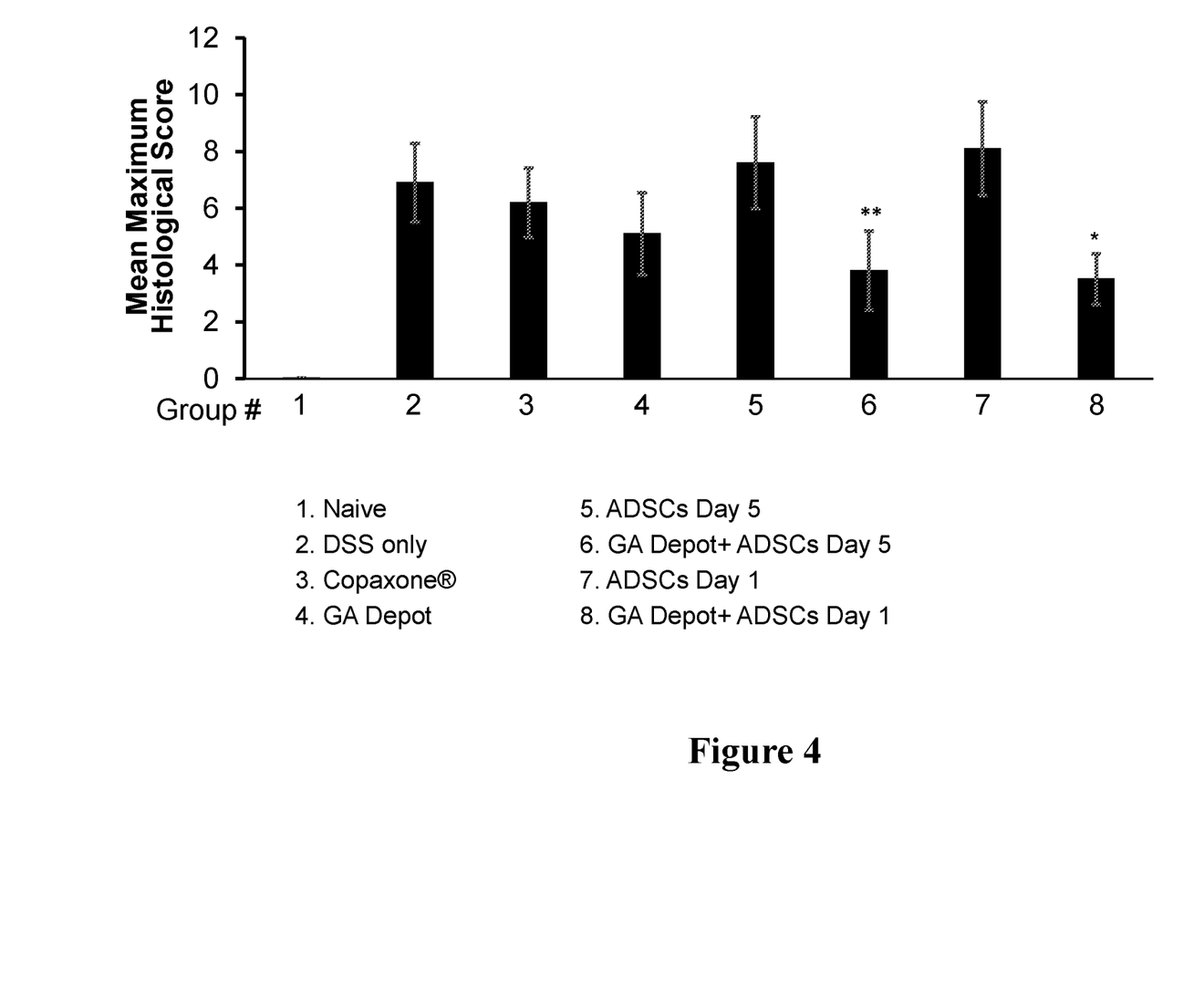
FIG. 4. Effect of GA Depot and ADSCs on DSS-induced IBD as determined by histological scoring. *$P<0.05$ compared to all groups except GA Depot and GA Depot+ADSCs Day 5; **$P<0.05$ compared to ADSCs Day 1 and ADSCs Day 5. Single-factor analysis of variance (ANOVA) followed by one-tailed two-sample T test assuming unequal variances, n=10 (3 for naïve group), data presented as mean±standard error.

Histological score: The results are summarized in FIG. 4. The GA Depot+ADSCs groups showed significantly lower mean histological score than all other treatment groups, including Copaxone®.

To conclude, addition of DSS to animal's drinking water induced moderate IBD. Under the experimental conditions selected here, the use of Copaxone® had almost no effect on IBD manifestations. GA Depot alone or ADSCs alone showed some effect which was not statistically significant. In contrast, the use of GA Depot in combination with ADSCs decreased all IBD manifestations in a statistically significant manner. It reduced weight loss, prevented rectal bleeding in most of the animals and prevented shortening of the colon. It also decreased DAI (combined measurement of weight change, stool consistency and bleeding) and histological score. The beneficial effects were observed even when the cells were administered five days after IBD induction. Taken together, the data suggests a high therapeutic effect of GA Depot and ADSCs in inflammatory bowel disease.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method of reducing severity of one or more ulcerative colitis symptoms in a subject, wherein the one or more symptoms are selected from the group consisting of rectal bleeding, colon length shortening and colonic histological changes, the method comprising administering to the subject a combination of (i) a pharmaceutical composition comprising glatiramer acetate in a sustained release depot form, wherein the sustained-release depot form is a poly (D,L-lactide-co-glycolide) (PLGA)-based injectable depot, and wherein the amount of glatiramer acetate in the pharmaceutical composition is between 20 to 100 mg; and (ii) human adipose-derived stem cells (hADSCs), wherein $10^6$-$10^7$ hADSCs are administered to the subject per one administration.

2. The method of claim 1, wherein the pharmaceutical composition comprising glatiramer acetate is formulated for intramuscular administration and the administering is via intramuscular injection.

3. The method of claim 1, wherein the pharmaceutical composition comprising glatiramer acetate is formulated for subcutaneous implantation, and the administering is via subcutaneous injection.

4. The method of claim 1, wherein administering the hADSCs is via systemic administration.

5. The method of claim 4, wherein the systemic administration is selected from the group consisting of intraperitoneal, intravenous and intramuscular injections.

6. The method of claim 1, wherein administering the hADSCs is via local administration.

7. The method of claim 1, wherein the hADSCs are derived from human subcutaneous fat obtained by liposuction aspiration.

8. The method of claim 1, wherein the hADSCs are autologous.

9. The method of claim 1, wherein the hADSCs are allogeneic.

10. The method of claim 1, wherein the hADSCs are characterized by positive expression of CD44, CD73 and CD90 by at least 95% of the cells, positive expression of CD105 by at least 90% of the cells, and negative expression of CD45, CD19, CD11B and HLADR by at least 95% of the cells.

11. The method of claim 10, wherein the hADSCs are further characterized by positive expression of CD34 by 0.1-10% of the cells.

12. The method of claim 1, wherein the glatiramer acetate comprises the acetate salt of L-alanine, L-glutamic acid, L-lysine, and L-tyrosine in the molar ratios of about 0.14 glutamic acid, about 0.43 alanine, about 0.10 tyrosine and about 0.33 lysine.

13. The method of claim 1, wherein the glatiramer acetate comprises about 15 to about 100 amino acids.

14. The method of claim 1, wherein the pharmaceutical composition comprising glatiramer acetate is in the form of microparticles prepared by a water-in oil-in water double emulsification process.

15. The method of claim 1, wherein the pharmaceutical composition comprising glatiramer acetate comprises an internal aqueous phase comprising a therapeutically effective amount of glatiramer acetate, a water immiscible polymeric phase comprising PLGA and an external aqueous phase.

16. The method of claim 15, wherein the external aqueous phase comprises a surfactant selected from polyvinyl alcohol (PVA), polysorbate, polyethylene oxide-polypropylene oxide block copolymers and cellulose esters.

17. A method of delivering a combination of (i) a pharmaceutical composition comprising glatiramer acetate in a sustained release depot form, wherein the sustained-release depot form is a poly (D,L-lactide-co-glycolide) (PLGA)-based injectable depot; and (ii) human adipose-derived stem cells (hADSCs) to a subject in need thereof, comprising injecting $10^6$-$10^7$ hADSCs and 20 to 100 mg glatiramer acetate in the sustained release depot form to the subject per injection, wherein the subject is at risk of rectal bleeding and colon shortening, or experiencing rectal bleeding and/or colon shortening.

* * * * *